United States Patent [19]
Kelly et al.

[11] 4,075,318
[45] * Feb. 21, 1978

[54] SKIN PROTECTIVE COMPOSITIONS

[75] Inventors: Ralph Kelly, Cincinnati; Edmond Jean Ritter, Loveland, both of Ohio

[73] Assignee: Cincinnati Milacron, Inc., Cincinnati, Ohio

[*] Notice: The portion of the term of this patent subsequent to Oct. 30, 1990, has been disclaimed.

[21] Appl. No.: 46,561

[22] Filed: June 15, 1970

Related U.S. Application Data

[63] Continuation-in-part of Ser. No. 696,509, Jan. 9, 1968, Pat. No. 3,630,934, which is a continuation-in-part of Ser. No. 613,095, Feb. 1, 1967, Pat. No. 3,538,009.

[51] Int. Cl.² ............................................. A61K 7/06
[52] U.S. Cl. ...................................... 424/70; 424/78; 424/317
[58] Field of Search .................. 424/70, 317, 78, 316, 424/365; 106/243, 252

[56] References Cited

U.S. PATENT DOCUMENTS

| | | | |
|---|---|---|---|
| 1,913,631 | 6/1933 | Graves | 424/316 |
| 2,129,836 | 9/1938 | Goodman | 424/365 |
| 3,100,784 | 8/1963 | Goebel | 260/407 |
| 3,157,629 | 11/1964 | Patrick, Jr. | 260/407 |
| 3,493,534 | 2/1970 | Coury et al. | 260/407 |
| 3,538,009 | 11/1970 | Kelly et al. | 252/546 |
| 3,630,934 | 12/1971 | Kelly et al. | 424/343 |
| 3,769,242 | 10/1973 | Kelly et al. | 252/542 |

FOREIGN PATENT DOCUMENTS 6,513,582   5/1966   Netherlands.

OTHER PUBLICATIONS

Sagarin, Cosmetic - Science & Technology, (1957), Interscience Publishers, N. Y., pp. 81, 82, 87, 93–102, 108, 111, 115, 117, 118, 119, 120, 121, 123, 125, 128–130, 137–139, 149, 150, 159–160, 162–167.

*Primary Examiner*—Dale R. Ore
*Attorney, Agent, or Firm*—Plumley and Tyner

[57] ABSTRACT

Compositions effective for protecting the skin from dermatologic irritation are formed by incorporating a protective agent which is an organic compound containing two or more polar groups, e.g. carboxyl groups, which are separated by at least 15 atoms the majority of which are carbon atoms and preferably containing a cyclic moiety of at least 5 atoms, e.g. the dimer of linoleic acid, in a pharmaceutically acceptable base.

11 Claims, No Drawings

SKIN PROTECTIVE COMPOSITIONS

CROSS REFERENCES TO RELATED APPLICATIONS

This application is a continuation-in-part of Ser. No. 696,509 filed Jan. 9, 1968, now U.S. Pat. No. 3,630,934 issued Dec. 28, 1971, which in turn is a continuation-in-part of application Ser. No. 613,095 filed Feb. 1, 1967 now U.S. Pat. No. 3,538,009 issued Nov. 3, 1970.

BACKGROUND OF THE INVENTION

A great many chemical compounds are known to cause dermatologic irritation of the skin upon contact. The reaction of the skin to such contact can range from a simple reddening and drying, as is common following repeated contact with detergent solutions during dishwahing and housework, to very severe blistering of the skin. The usefulness of a great many chemical compounds is severely limited because of their tendency to cause skin irritation.

The cause for this irritation is not clearly understood, but it is believed that a number of irritants have a denaturing effect on the keratin layer of the skin. As a result, other chemicals which normally do not irritate the skin will cause irritation when combined with, or applied to the skin following contact with some material which causes denaturation.

It is, therefore, an object of the present invention to prevent or reduce skin irritation resulting from contact of the skin with chemical compositions.

It is another object of the present invention to modify the protein-keratin layer of the skin to prevent or reduce skin irritation when contacted with chemical compositions which irritate the skin.

It is a further object of this invention to provide protective compositions which may be applied to the skin to prevent irritation from subsequent contact with irritating agents.

It is a still further object of this invention to provide protective hand-lotions and creams which are effective in preventing dermatologic reaction of the skin due to excessive exposure to water or to irritating chemicals.

SUMMARY OF THE INVENTION

According to the invention, skin irritation is prevented or reduced by applying to the skin prior to contact with an irritant, a protective agent which can be generalized as an organic compound containing at least two polar groups which are separated by a chain of at least 15 atoms a majority of which are carbon atoms and preferably containing a cyclic moiety of at least 5 atoms. The protective agent is dispersed in a pharmaceutically acceptable base, such as the type used in hand-lotions and hand-creams.

As used herein, the term "polar group" is meant to define a group having a dipole moment and containing at least one nitrogen, oxygen, phosphorus, sulfur or combinations thereof. These groups are deemed to be capable of hydrogen bonding with the protein, although the formation of stronger bonds such as covalent bonds is not excluded. The cyclic moiety is preferably a carbocyclic, i.e. cyclic hydrocarbon moiety of 5 to 18 carbon atoms which can be saturated or can contain from 1 to 9 double bonds and can contain one or more substituents on the ring. Heterocyclic moieties which contain the structures —O—, —S—, —N—, or —NH— in the ring can also be present in the mildness additive and serve as the necessary cyclic moiety. Hetero-atoms are useful.

In accordance with the present invention, it has been discovered that skin irritation and other more severe forms of dermatitis caused by the contact of chemicals with the skin can be reduced or eliminated by contacting the skin with the compounds of the general formula above prior to contact with a dermatologic irritant. Rinsing of the skin with water or a mild soap solution after application of the protective compound but prior to the application of the irritant does not cause a significant change in the effect of the protective agent when a skin irritant is subsequently contacted. This and other types of evidence, such as electrophoretic studies of mixtures of soluble proteins and protective agents have shown that some form of interaction occurs between the keratin layer of the skin and the protective agents. Although the complex formed between protein molecules and the protective agent can be isolated by the indicated electrophoresis, the specific nature of the complex has not yet been established. It is presumed, however, that both adsorption and some form of chemical interaction are involved. It is further theorized that the cyclic structure in the protective agent aids in the adsorption of the protective agent onto the keratin layer of the skin and that the polar groups of the protective agent interact with the protein molecules of the keratin layer. In addition to the requirement that the protective agent contain at least two polar groups, the polar groups of the protective agent must also be separated by a chain of at least 15 atoms, a majority of which should be carbon atoms. However, the presence of additional polar groups located intermediary to the described two terminal polar groups does not appear to interfere in the effectiveness of the protective agent. It is believed that as a result of this chain length the indicated polar groups are capable and do interact with different protein molecule. The irritation of the skin by the action of a detergent or other irritant is believed to be caused by the penetration of the detergent into the skin, causing separation and/or degradation of the protein molecules of the keratin layer, thereby exposing the living cells of the skin to the detergent and, more significantly, exposing these cells to other, more irritating compounds associated with the detergent. The damage to the cells caused by the contact is believed to result in irritation, inflammation, and dermatitis. The protective agents employed in the compositions of the present invention are believed to counteract this breakdown by providing additional bridges between the protein molecules of the keratin layer, which maintain the integrity of the skin surface, thereby preventing the penetration of detergent or other irritant molecules through the keratin layer into the living tissue. It is to be understood, however, that we do not wish to be bound by the foregoing explanation of the activity of the protective agents of the present invention, and that such explanation is only set forth for a better understanding of the present invention.

The protective agents of the present invention contain at least two polar groups separated by an organic radical of at least 15 atoms, a majority of which are carbon and which contain a cyclic group. Additional polar groups may be present in this divalent radical or may be located on branches attached to this radical. Such additional polar groups do not interfere in the effectiveness of the protective agent. The two polar groups described can be the same or different. Suitable polar groups include hydroxyl (—OH); carboxyl (—COOH); ester (R'O—CO—, wherein R' can be an aliphatic, cycloaliphatic, or aromatic radical of 1-12 carbon atoms, or can be part of a polyester chain); amino (—NH$_2$); substituted amino (NHR" or —NR"R'", wherein R" or R'" are aliphatic or aromatic hydrocarbon radicals of 1-12 carbon atoms, or wherein R" and R'" can combine to form 3- to 6-membered rings with the nitrogen, or wherein R" is part of a polyamine chain); amido

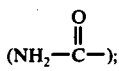

substituted amido

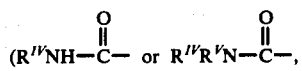

wherein R$^{IV}$ and R$^{V}$ are aliphatic or aromatic hydrocarbon radicals of 1-12 carbon atoms and R$^{IV}$ can be part of a polyamide chain); quaternary ammonium salts

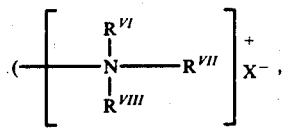

where R$^{VI}$, R$^{VII}$, and R$^{VIII}$ are lower alkyl radicals and X is an anion such as a halogen ion); sulfate (—SO$_4$Me, where Me is a metal and preferably an alkali metal); sulfonate (—SO$_3$Me); sulfonamide (—SO$_2$NH$_2$); substituted sulfonamide (—SO$_2$NHR$^{IV}$ or —SO$_2$NR$^{IV}$R$^{V}$); thio acid salts (—COSMe); thioesters

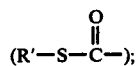

sulfoxides (=SO); sulfonic acid (—SO$_3$H); sulfinic acid (—SO$_2$H); phosphate (—HMePO$_4$ or —Me$_2$PO$_4$); and phosphonium salts (—HPO$_3$Me). The preferred polar groups employed in the protective agents of the present invention are those which contain, aside from any metal or halogen which may be associated with the polar group in ionic form, carbon and oxygen or carbon and nitrogen. In general functional groups of greater polarity are preferred over those of lesser polarity. It will be apparent that the size of any of the described substituents and particularly hydrocarbon substituents on the polar group will affect the polarity. In general, the preferred substituents on the polar groups are lower alkyl groups and such water-solubilizing groups as polyoxyalkylene radicals, in particular polyethylene glycol chains.

The effectiveness of the protective agents in preventing skin irritation not only requires the presence of at least two polar groups in the protective agent but also the separation of the polar groups by an atom chain of at least 15 atoms, the majority of which are carbon atoms. The presence of additional polar groups does not interfere in the function of the two polar groups separated by the necessary number of atoms, regardless of whether these polar groups are part of such chain or located on side branches of the molecule. The presence of more than two polar groups each of which are separated by 15 or more atoms increases the effectiveness of a protective agent in which the polar groups are weak polar groups, such as hydroxyl groups, but does not appear to add significantly to the effectiveness of a protective agent containing at least two strong polar groups such as carboxyl groups separated by the necessary linking chain.

Although the minimum size of the linking radical is determined by the length of the chain separating the polar groups, the maximum size of the linking radical is determined by the dispersibility of the protective agent in the medium in which it is incorporated. Thus, compounds which are not liquid or colloidally dispersible are not suitable in preventing skin irritations. Hence, the upper limit of the size of the linking radical is determined not only by the number of atoms in the linking radical, but also by the presence of additional polar groups in the linking radical which can increase the dispersibility of the protective agent, as well as the nature of any radical attached to the polar group. In general, however, the linking radical contains less than 80 atoms. As indicated, the linking radical has, preferably, a carbon backbone structure which can be aliphatic, cycloaliphatic, or aromatic in nature. The required carbocyclic or heterocyclic moiety need not be part of the backbone structure. Particularly effective are hydrocarbon linking radicals which contain a cycloaliphatic or aromatic ring structure. In addition to the preferred hydrocarbon structure, the linking radical can also be in the form of a polymeric structure such as a polyester, polyether, polyamide, or polyamine. Although other polymer linking radicals will be apparent to those skilled in the art, many of these radicals are excluded by virtue of the limitations with respect to solubility of colloidal dispersibility required to give rise to the protective properties.

The following classes of materials are protective agents suitable for use in the present invention.

A. The polymerized product of 2 to 4 molecules of a monomeric C$_{12}$ to C$_{26}$ fatty acid, said product containing 2 to 4 carboxyl groups; or in place thereof derivative radicals selected from the group consisting of carboxyl salt; hydroxyl; unsubstituted amino; substituted amino wherein the substituents are aliphatic or aromatic hydrocarbon radicals of 1 to 12 carbon atoms, or said substituents taken together form a 3 to 6 membered carbocylic or heterocyclic ring with the amino nitrogen; unsubstituted amido; substituted amido wherein the substituents are aliphatic or aromatic hydrocarbon radicals of 1 to 12 carbon atoms, or said substituents taken together form a 3 to 6 membered carbocyclic or heterocyclic ring with the amido nitrogen; quaternary ammonium wherein the nitrogen substituents are alkyl of 1 to 6 carbon atoms; lower alkyl ester; sulfate; sulfonate; phosphate; phosphonate; and derivative compounds containing further substituents in said alkyl, aliphatic or aromatic hydrocarbon radicals selected from the group consisting of carboxyl and the said derivative radicals.

Among the cationic protective agents defined in A which can be utilized in this invention are fat polyquaternary ammonium compounds having the formula:

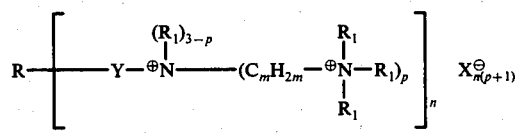

in which
- R is the hydrocarbon radical of the polymeric fat acids, $R(COOH)_n$ obtained by polymerization of an unsaturated higher fatty acid containing 12 to 26 carbon atoms;
- $R_1$ is an aliphatic hydrocarbon group having from 1 to 6 carbon atoms;
- X is an anion;
- Y is an alkylene radical having 1 to 8 carbon atoms;
- m is 3 or 4;
- n is 2 or 3; and
- p is 0, 1, or 2.

The polymeric fat acids from which the quaternary ammonium compounds employed as protective agents in the present invention are derived are polymerization products of unsaturated fatty acids containing from 12 to 26 carbon atoms and generally having a degree of polymerization of two to four. Quaternary ammonium compounds prepared from fatty acid mixtures containing such dimer, trimer, or tetramer acids are also useful. Quaternary ammonium compounds of the type useful in the present invention are disclosed in U.S. Pat. Nos. 3,073,864 and 3,299,138, the disclosure of which patents is incorporated herein by reference.

B. Esters and polyesters of cycloaliphatic or aromatic polycarboxylic acids containing at least one 5 to 7 carbon ring and polyoxyalkylene ethers containing 2 to 30 oxyalkylene units in which the alkylene radical contains 2 to 4 carbon atoms. The benzene, naphthalene, cyclohexane, cyclopentane, cycloheptane, and diphenyl polycarboxylic acids are suitable. Among the preferred polycarboxylic acids are the benzene di-, tri-, and tetra-carboxylic acids, the corresponding dihydrobenzene (cyclohexadiene), tetrahydrobenzene (cyclohexene), and cyclohexane polycarboxylic acids. The degree of polymerization can vary widely so long as the requirements that the compounds contain at least 15 carbon atoms between the polar groups and the proper solubility or dispersibility characteristic in aqueous media are maintained. The polyoxyalkylene ether can contain further substituents such as shown in Compounds 45 and 49 in Example 1.

C. Condensation products of alkylene oxides having 2 to 4 carbon atoms and polyamines having 2 to 4 amino groups and containing 2 to 8 carbon atoms in an aliphatic, cycloaliphatic or aromatic group. The alkylene oxide addition units can comprise block or random copolymer units.

Polymers having the following formula have been found to be useful in the practice of this invention:

$$\begin{matrix} H(C_2H_4O)_y(C_3H_6O)_x & & (C_3H_6O)_x(C_2H_4O)_yH \\ & \diagdown N-CH_2-CH_2-N \diagup & \\ H(C_2H_4O)_y(C_3H_6O)_x & & (C_3H_6O)_x(C_2H_4O)_yH \end{matrix}$$

in which x is from about 2 to about 10, and y is from about 2 to about 15.

D. Condensation products of ethylene oxide with a hydrophobic base formed by the condensation of propylene oxide with propylene glycol, having the general formula:

$$HO(CH_2CH_2O)_a(CHCH_2O)_b(CH_2CH_2O)_cH$$
$$|$$
$$CH_3$$

wherein
- a is 1 to 150
- b is 15 to 70
and
- c is 1 to 150

E. Esters and polyesters of the polymerized fatty acid defined in A above and a polyol selected from the group consisting of
 (a) polyoxyalkylene ethers containing 2 to 30 oxyalkylene units in which the alkylene radical contains 2 to 4 carbon atoms;
 (b) condensation products defined in C and D above.

The protective agents described in A., B., and E., i.e. those which must contain a cyclic moiety, are preferred over those of C. and D., which do not necessarily contain a cyclic moiety.

The most preferred protective agents are those of A. above, the polymerized, ethylenically unsaturated $C_{12}$ to $C_{26}$ fatty acids and polar group-containing derivatives thereof. Generally, the polymerized fatty acids contain from 2 to 4 monomeric acid units, and, consequently, from 2 to 4 carboxyl groups. The polymeric fatty acids can be employed as protective agents, as such, or the carboxyl groups can be altered by known chemical reactions into other polar groups, such as by esterification, amidation, and the like. The polymerization of ethylenically unsaturated fatty acids into dimer, trimer, and tetramer acids is known in the art and generally results in a cycloaliphatic ring structure. Thus, the dimer acid derived from linoleic acid has the structure, which can exist in the cis and trans forms, of $$HOOC-(CH_2)_7-\underset{\underset{CH_2(CH_2)_4-CH_3}{|}}{\overset{CH}{\underset{CH}{\overset{CH}{\diagup}}\diagdown\underset{CH}{\overset{CH-CH_2-CH=CH-(CH_2)_7-COOH}{\diagup}}}}$$

The dimer, trimer, and tetramer acids are commercially available. It will be apparent, in view of the foregoing discussion, that the protective agents need not be pure, but that a mixture of protective agents can be employed, such as a mixture of dimer and trimer acids, and that the protective agent can, furthermore, contain compounds which do not add to the protective properties of the protective agent, such as unpolymerized fatty acids. Various polar groups can be substituted for the carboxyl groups of polymerized fatty acids as described above. Hydrogenated derivatives are also contemplated.

The concentration of the protective agent in the compositions of this invention can vary widely, depending on the nature of the base in which it is dispersed and other factors. Generally, concentrations of about 0.1 to 20% by weight, more often about 0.5 to 10% by weight, are used.

The protective agents of this invention exhibit a protective effect against a wide range of chemical irritants. The compositions of this invention may, therefore, be applied to the skin prior to anticipated contact with a detergent or soap solution, organic solvents, petroleum products, paints, cutting fluids, and a great many other irritants.

For application to the skin, the protective agents are incorporated into a pharmaceutically acceptable base to form either a lotion or a cream. While there are a great many formulas for the production of such lotions or creams, most such compositions are emulsions comprising an emulsifier such as triethanolamine stearate or glycerol mono stearate; an emollient such as lanolin, cetyl, alcohol, or stearyl alcohol; a humectant such as glycerine, sorbitol, mannitol, or the glycols, and various vegetable oils or perfuming agents. Although most creams and lotions today are of the emulsion type, the protective agents of our invention can also be added to the older hand balms, formed of a gum, such as gum tragacanth, in water.

The protective agents of this invention can be incorporated into hand lotions or creams which contain other known protective agents, such as fatty acids for protection against dry dust, and petroleum jelly or waxes for protection against aqueous solutions; methyl cellulose and cellulose derivatives for protection against solvents, oils and fats.

PREFERRED EMBODIMENTS OF THE INVENTION

In the preferred embodiments, one of the protective agents falling within the generic formula is incorporated into a standard cream base, or into a lotion. The protective agents falling within the generic formula which are currently most preferred are those based upon the dimer acids. In particular, we have found that the dimer acids which have been esterified with various alcohols, and particularly with oxyalkylene group-containing alcohols, are the most efficacious. However, since certain of the protective agents display different degrees of success in protecting against various irritants, our invention must be construed as encompassing all of the compounds falling within the above-stated genus. While the examples below set forth the use of compounds which are effective against specific chemical irritants, it should be understood that other compounds falling within the genus may be more effective against other specific irritants.

EXAMPLE 1

This example illustrates several of the methods which are used to determine whether a given chemical substance possesses activity as a protective agent for keratin, and lists representative materials which have been determined to have such activity based on one or more of the described tests.

Several of the listed protective agents have been tested by each of the methods described below and a number of protective agents have been subjected to at least two of the tests. Good correlation of results has been found between the various tests.

A. ANIMAL IMMERSION TEST

A female, albino guinea pig, weighing about 300 to 325 g, is immersed up to the thoracic region in the test solution at 40° C for 4.5 hours per day on three successive days. Each animal is thoroughly rinsed and dried after each immersion. Three days after the last immersions, the skin of each animal is examined for gross changes, and grades are assigned which represent the degree of damage to the skin. In general, three animals are tested simultaneously in the same solution. The grading system is based on a scale of 1 to 10, in which the numbers have the following meanings.

| Grade or Rating | Gross Reaction | Skin Damage |
|---|---|---|
| 1 | Severe cracking and bleeding; death of animal in most instances | Extremely severe; death of skin tissue |
| 2 | Severe cracking; moderate bleeding | " |
| 3 | Severe cracking; slight to moderate bleeding | Severe |
| 4 | Moderate cracking | " |
| 5 | Slight cracking | Moderate |
| 6 | Severe scaling | " |
| 7 | Edema; slight to moderate scaling | " |
| 8 | Slight scaling and moderate edema | Slight |
| 9 | Slight redness and edema | " |
| 10 | Normal | Normal |

Despite the fact that this exposure test is conducted using extremely dilute solutions, it is an exaggerated test, as compared to human exposure; although it has been established (see Canadian Patent 639,398) that the test correlates extremely well with the skin irritation effect observed on human skin.

In preparing the test solution, a 100 g concentrate is first prepared which is then employed in the test solution in 1% by volume concentrations. In order to prepare a homogeneous concentrate which is readily dilutable, the following additional ingredients were added as indicated: Igepal CA-630, a commercially available nonionic wetting agent of octylphenoxy-poly(oxyethylene)ethanol; triethanol amine, and capric acid. The triethanol amine (TEA) is employed to allow salt formation of mildness additives employed in combination with anionic detergents and the capric acid (Cap. A.) is employed for the same purpose in combination with cationic detergents. In general, the irritant and the protective agent are each employed in the examples illustrated below in a concentration of 15 weight percent based on the described 100 g concentrate.

A difference of about 2 units between the control animal (immersed in irritant) and the test animal (immersed in irritant containing protective agent) under the given conditions is generally considered to indicate a satisfactory protective effect.

A typical irritant used in the above-described test is sodium lauryl sulfate, but a variety of irritant materials have been used, including alkali, such as sodium and ammonium hydroxide, and oxidants such as hydrogen peroxide. In general, a material which exhibits protective properties with a given irritant is found to exhibit similar properties with other irritants.

Further details of the above-described test are found in Ser. No. 696,509 filed Jan. 9, 1968 and Ser. No. 613,095 filed Feb. 1, 1967, the disclosure of which is incorporated herein by reference.

B. OCCLUSIVE PATCH TEST (a modified version of the Finkelstein patch test)

Female albino guinea pigs, weighing between 280 and 320 grams are shaved, and one application of 7.4% formalin applied. A quantity of 0.15 milliliters of each protective agent is applied to part of the test area and rubbed into the skin approximately 10 times in each direction. After a drying time of one-half hour, a solution of the irritant is applied to a test pad which is placed over the test site and secured by tape. The pad and tape is then covered by a plastic sheet which is secured at the extremes of the abdominal area. 2.0 cc of trypan blue dye PPS was injected into each axila of the test animal. After 18 hours, the pads were removed and the test sites examined for degree of intensity of the dye which had accumulated at the test site. Dye accumulation was evaluated on the scale of 0 to 100, 0 being the intensity of dye when no protective agent was applied, and 100 being no visible dye accumulation. Variations of dye intensity of about 5% or more between test and control is considered significant. The following scale is also used to interpret results:

| Rating scale | (% Protectability) |
|---|---|
| 80–100 | Excellent |
| 70–80 | Good |
| 60–70 | Minimal |
| 50–60 | Irritating |
| 0–50 | Very irritating |

C. ELECTROPHORESIS

The prescribed procedure for paper electrophoresis is followed. This involves placing a sample on a paper strip, mounting the strips in a closed cell filled with a buffer (pH 8.6 most often used), and connecting the apparatus to a power supply. Thus, degree of mobility of the sample along the strip in a given time can be measured. When applied to keratin, protective agents and skin irritants or agents which degrade keratin samples, the degree of mobility indicates that an interaction takes place between protein and the protective agent, since this combination exhibits a mobility less than keratin alone. The combination of keratin and skin irritant or keratin and an agent which degrades protein, on the other hand, exhibits a mobility greater than protein. The differences in degree of mobility are indicative of the efficacy of the protective agent.

D. MICROSCOPIC STUDIES

Keratin, particularly hair, is subjected to a degradating agent with and without pretreatment with, or incorporation of, a potential protective agent. Protective qualities are evidenced by reduced physical deterioration, especially scaling.

The following materials have been found to possess protective qualities for keratin by one or more of the methods described above.

In the formulae listed below "D" represents the carboxyl free radical of dimer acid (dimerized linoleic acid) and "T" represents the carboxyl free radical of trimer acid (trimerized linoleic acid).

1. HO—[(CH₂—CH₂—O)ₘ—CO—[D]—CO₂]ₓH $m = 2$ to 30; $x = 1$ to 10

2. HOCH₂—[D]—COOH

3. NaOOC—[D]—COONa

4. [D]—(CH₂—NH—CH₂—CH₂—NH₂)₂

5. [D]—(CH₂—NH—CH₂—CH₂—CH₃)₂

6. [T]—(COOH)₃

7. [T]—(CONH₂)₃

8. [T]—(COONa)₃

9. [T]—(SO₄Na)₃

10. [T]—(CH₂NH₂)₃

11. Reaction product of dimer acid and hydroxyethyl ethylene diamine. The product is shown as a diester but consists of a mixture of ester, half ester-half amide, diamide and oxazoline.
    NH₂—(CH₂)₂—NH—(CH₂)₂OOC—[ D ]—COO(CH₂)₂—NH—(CH₂)₂—NH₂

12. Reaction product of dimer acid and N-amino-propyl diethanolamine. The product is shown as the diamide, but contains also the ester and ester-amide.

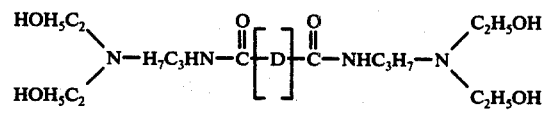

13. Dimer acid or soap thereof
    [D]—[COOX]₂ wherein X is H, Na, K, or
    —C₂H₅N(C₂H₅OH)₂

14. Polyester of polypropylene glycol and dimer acid

[D]—[COO(C₃H₆O)ₓOC—[D]—COO(C₃H₆O)ₓH]₂

$x =$ about 6 to about 25

15. Ester of polybutylene glycol and dimer acid

[D]—[CO(OC₄H₉)ₓH]₂

$x =$ 10 to 20

16. Dimer tetramine
    [D] [CH₂—NH—CH₂—CH₂—CH₂—NH₂]₂

17. Tetramethyl dimer diamine

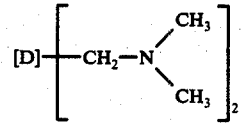

18. Mixed ester of reaction of pyromellitic anhydride with octylphenoxypolyethoxyethanol and subsequent reaction with the polyol resulting from reaction of ethylene and propylene oxides with ethylene diamine.

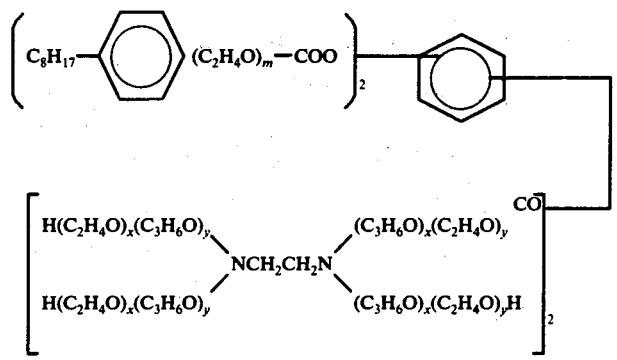

$x =$ about 7, $y =$ about 9, $m =$ 4 to 10

19. Tetrakis-(3-carb-octylphenoxypolyethoxybenzoyl) ester of the tetrol resulting from ethylene oxide and propylene oxide addition to ethylene diamine.

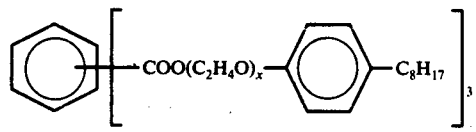

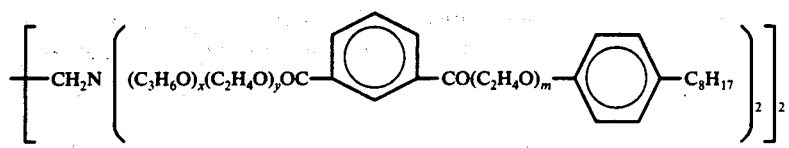

$x =$ about 7
$y =$ about 9
$m =$ 4 to 10

20. Terephthalic acid ester of polyethylene glycol

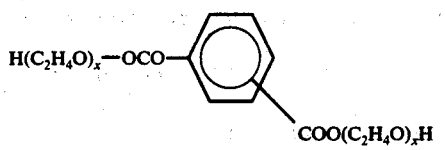

$x$ is 4 to 25

21. Tetrahydrophthalic acid ester of polyethylene glycol

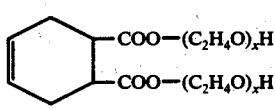

$x =$ 4 to 25

22. p-Pyromellitic acid ester of polypropylene glycol

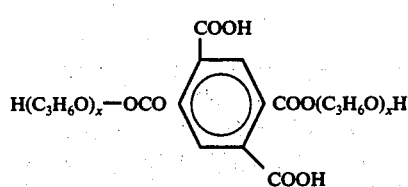

$x =$ 5 to 8

23. Tris(octylphenoxypolyethoxyethyl) trimesate

24. The tetrol resulting from block addition of propylene oxide and ethylene oxide to ethylene diamine.

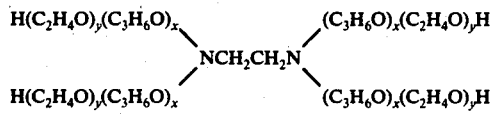

$x$ is about 7
$y$ is about 9

$$HO(CH_2CH_2O)_a(CHCH_2O)_b(CH_2CH_2O)_cH \quad\quad 51.$$
$$| \atop CH_3$$

$a =$ 1 to 150
$b =$ 15 to 70
$c =$ 1 to 150

The following examples illustrate the preparation of creams and lotions according to the invention.

EXAMPLE 2

A cold cream type formula is prepared according to the following formula:

| Ingredients | % |
| --- | --- |
| Dimer Acid | 2.0 |
| Beeswax | 8.0 |
| Petroleum Jelly | 15.0 |
| Mineral Oil | 25.0 |
| Lanolin | 13.5 |
| Glyceryl mono stearate | 2.0 |
| Borax | 0.5 |
| Water | 34.0 |
| Perfume and Preservative | q.s |

EXAMPLE 3

A low lanolin content cold cream has the following formula:

| Ingredients | % |
|---|---|
| Diester of Dimer Acid and Tetronic 504* | 1.5 |
| Lanolin | 3.0 |
| White Oil | 3.0 |
| Petroleum Jelly | 3.0 |
| Beeswax | 14.0 |
| Sorbitol Syrup | 3.0 |
| Glycerin | 3.0 |
| Water | 69.5 |
| Perfume and Preservative | q.s |

*This is Compound 50 in Example I

EXAMPLE 4

A cream base is formed according to the following formulation:

| Ingredients | % |
|---|---|
| The polymer of equal portions of pyromellitic acid and polypropylene glycol 400 having an average molecular wight of about 1054 | 1.0 |
| Glyceryl mono stearate (self-emulsifying) | 14.0 |
| Lanolin | 2.0 |
| Cetyl Alcohol | 2.0 |
| Mineral Oil | 8.0 |
| Spermaceti | 5.0 |
| Almond Oil | 8.0 |
| Glycerin | 5.0 |
| Water | 55.0 |
| Perfume and Preservative | q.s |

EXAMPLE 5

A lotion containing gum tragacanth and containing no fatty matter is formulated as follows:

| Ingredients | % |
|---|---|
| Dimer diamine | 3.0 |
| Gum tragacanth | 2.0 |
| Glycerin | 10.0 |
| Titanium Dioxide | 0.2 |
| Water | 85.8 |
| Perfume and Preservative | q.s |

EXAMPLE 6

A lotion displaying pearliness has the following formulation:

| Ingredients | % |
|---|---|
| Triethanolamine soap of Dimer Acid | 3.0 |
| Cetyl Alcohol | 0.5 |
| Lanolin | 1.5 |
| Petroleum Oil | 14.0 |
| Stearic Acid | 4.0 |
| Isopropyloamines | 0.8 |
| Glycerin | 5.0 |
| Methyl-p-hydroxy-benzoate | 0.2 |
| Titanium dioxide | 0.1 |
| Distilled water | 72.4 |
| Perfume and Preservative | q.s |

EXAMPLE 7

A lotion containing polyvinyl pyrrolidone to form a film resistant to penetration by solvents, oil and fats is as follows:

| Ingredients | % |
|---|---|
| Polymer of terephthalic acid and polyethylene glycol 1000 | 1.0 |
| Glyceryl mono stearate | 8.0 |
| Magnesium stearate | 14.0 |
| Beeswax | 3.0 |
| Petrolatum | 10.0 |
| Mineral Oil | 5.0 |
| Water | 56.0 |
| Polyvinylpyrrolidone | 1.0 |

EXAMPLES 8-10

The various formulations are evaluated for their protective ability by a modified version of the Finkelstein (Occlusive Patch) test. Female albino guinea pigs weighing between 280 and 320 grams are shaved, and one application of 7.4% formalin applied. A quantity of 0.15 millimeters of each test lotion is applied to the test area and rubbed into the skin approximately 10 times in each direction. After a drying time of one-half hour, an irritating cutting fluid emulsion comprising anionic surfactants, salts and oil, is applied to a test pad which is placed over the test site and secured by tape. The pad and tape is then covered by a plastic sheet which is secured at the extremes of the abdominal area. 2.0 cc of Trypan blue dye PPS (physiological saline solution, 0.85 NaCl in $H_2O$) was injected into each axila of the test animal. After 18 hours, the pads were removed and the test sites examined for degree of intensity of the dye which had accumulated at the test site. Dye accumulation was evaluated on the scale of 0 to 100, 0 being the intensity of dye when no location of any sort was applied and 100 being no visible dye accumulation. The following Table shows formulation of the three lotions containing protective agents and three control lotions.

TABLE I

| Ingredient | LOTIONS | | | | | |
|---|---|---|---|---|---|---|
| | A | B | C | D | E | F |
| Stearic Acid | 1.0 | 1.0 | 1.0 | 1.0 | 1.0 | 1.0 |
| Isopropyl ester of Lanolin | — | — | 1.4 | 1.4 | — | — |
| Glycerin | 0.2 | 0.2 | 0.2 | 0.2 | — | — |
| Propylene Glycol | 0.6 | 0.6 | 0.6 | 0.6 | — | — |
| Mineral Oil | 0.7 | 0.7 | — | — | — | — |
| 1-Monostearin | 0.8 | 0.8 | 0.8 | 0.8 | 2.0 | 2.0 |
| Hexadecanol | 0.2 | 0.2 | 0.2 | 0.2 | — | — |
| Isostearyl Alcohol | 0.4 | 0.4 | 0.4 | 0.4 | — | — |
| Petrolatum | 0.2 | 0.2 | — | — | — | — |
| Kelzan Gum | 1.0 | 1.0 | 1.0 | 1.0 | — | — |
| Hexachlorophene | 0.2 | 0.2 | 0.5 | 0.5 | 0.5 | 0.5 |
| Talc | 5.0 | 5.0 | 5.0 | 5.0 | 5.0 | 5.0 |
| Ethylene Diamine Tetracetic acid | — | — | — | — | 1.0 | 1.0 |
| Igepal DM 530* | — | — | — | — | 0.5 | 0.5 |

TABLE I-continued

| Ingredient | LOTIONS | | | | | |
|---|---|---|---|---|---|---|
| | A | B | C | D | E | F |
| Isopropyl myristate | — | — | — | — | 5.0 | 5.0 |
| Amerchol L-101** | 0.5 | 0.5 | — | — | — | — |
| 0.4% Carbopol *** 0.4% TEA in water | — | — | — | — | 34.5 | 34.5 |
| Polyethylene glycol 400 ester of dimer acid | 1.0 | — | — | — | — | — |
| Bis-hydroxyethyl dimerate | — | — | 3.0 | — | 3.0 | — |
| Water | 88.2 | 89.2 | 85.9 | 88.9 | 47.5 | 50.5 |

*Igepal DM 530 is Kialkylphenoxypoly(ethyleneoxy) ethanol.
**Amerchol L-101 is a multi-sterol extract containing highly surface active selected lanolin sterols and complex higher alcohols in their free forms only.
***Carbopol is a carboxy vinyl polymer of extremely high molecular weight, supplied in the acid form, requiring neutralization for optimum properties.

As can be seen from the Table I above, lotions A, C and E contain the protective agents and the lotions B, D and F are the respective controls for those lotions. In addition, animal tests were conducted with a nationally available commercial hand lotion available through retail drug and grocery outlets, identified herein as lotion G.

In order to obtain statistically valid results, each lotion was tested on from 5 to 12 animals and a statistical average of the test results calculated. Table II below shows the results for each of the above lotions.

| Rating Scale | (% Protectability) |
|---|---|
| 80-100 | Excellent |
| 70-80 | Good |
| 60-70 | Minimal |
| 50-60 | Irritating |
| 0-50 | Very irritating |

TABLE II

| Lotion | % Protectability |
|---|---|
| C | 80 |
| A | 73 |
| E | 73 |
| B | 64 |
| D | 61 |
| F | 54 |
| G | 54 |
| Irritating Chemical (emulsion containing anionic surfactants, salts and oil) | 0 |

What is claimed is:

1. A skin protective lotion or creme consisting essentially of emollient, humectant, surfactant and a protective agent in an amount effective to reduce the amount of skin irritation; said lotion or creme capable of reducing skin irritation compared to said lotion or creme without protective agent when applied to the skin prior to contact with a skin irritant; said protective agent selected from the group consisting of:

A. The polymerized product obtained from the polymerization of 2 to 4 molecules of a monomeric ethylenically unsaturated $C_{12}$ to $C_{26}$ fatty acid, said product containing 2 to 4 carboxyl groups; or in place of carboxyl groups derivative radicals selected from the group consisting of carboxyl salt; hydroxyl; unsubstituted amino; substituted amino wherein the substituents are aliphatic or aromatic hydrocarbon radicals of 1 to 12 carbon atoms, or said substituents taken together form a 3 to 6 membered carbocyclic or heterocyclic ring with the amino nitrogen; unsubstituted amido; substituted amido wherein the substituents are aliphatic or aromatic hydrocarbon radicals of 1 to 12 carbon atoms, or said substituents taken together form a 3 to 6 membered carbocyclic or heterocyclic ring with the amido nitrogen, quaternary ammonium wherein the nitrogen substituents are alkyl of 1 to 6 carbon atoms; lower alkyl ester; sulfate; sulfonate; phosphate; phosphonate; and derivative compounds containing further substituents in said alkyl, aliphatic or aromatic hydrocarbon radicals selected from the group consisting of carboxyl and the said derivative radicals;

B. esters and polyesters of cycloaliphatic or aromatic polycarboxylic acids containing at least one 5 to 7 carbon ring and hydroxy containing polyoxyalkylene ethers containing 2 to 30 oxyalkylene units in which the alkylene radical contains 2 to 4 carbon atoms;

C. esters and polyesters of the polymerized fatty acid product or the hydrogenated derivative thereof defined in A above and a hydroxy compound selected from the group consisting of
   (a) polyoxyalkylene ethers containing 2 to 30 oxyalkylene units in which the alkylene radical contains 2 to 4 carbon atoms; and
   (b) condensation products of alkylene oxides having 2 to 4 carbon atoms and polyamines having 2 to 4 amino groups and containing 2 to 8 carbon atoms in an aliphatic, cycloaliphatic or aromatic group.

2. The protective lotion or creme of claim 1 in which the protective agent is the diamine derivative of dimerized linoleic acid.

3. The skin protective lotion or creme of claim 1 wherein said protective agent is a polymerized product of 2 to 4 molecules of a monomeric $C_{12}$ to $C_{26}$ fatty acid containing 2 to 4 carboxyl or carboxyl salt groups.

4. The skin protective lotion or creme of claim 1 in which the protective agent comprises 0.1% to 20% by weight of the skin protective composition.

5. The skin protective lotion or creme of claim 1 in which the protective agent is as defined in paragraph A of claim 1.

6. The skin protective lotion or creme of claim 3 in which the protective agent is the triethanolamine salt of the polymerized product obtained from the polymerizatin of 2 to 4 molecules of a monomeric ethylenically unsaturated $C_{12}$ to $C_{26}$ fatty acid said product containing 2 to 4 carboxyl groups.

7. The protective lotion or creme of claim 5 in which the protective agent is the polymerized product obtained from the polymerization of 2 to 4 molecules of a monomeric ethylenically unsaturated $C_{12}$ to $C_{26}$ fatty acid containing unsubstituted amino groups instead of 2 to 4 carboxyl groups.

8. The skin protective lotion or creme of claim 1 in which said product of polymerization of 2 to 4 molecules of an ethylenically unsaturated $C_{12}$ to $C_{26}$ fatty acid comprises dimerized linoleic acid.

9. The skin protective lotion of claim 1 in which said protective agent is said acid defined in (A) or a salt thereof selected from the group consisting of Na, K and triethanolamine salts.

10. The skin protective lotion or creme of claim 1 in which said protective agent comprises dimerized linoleic acid, or the Na, K, or triethanolamine salt of dimerized linoleic acid.

11. The skin protective lotion or creme of claim 1 in which said protective agent is the triethanolamine salt of the dimer of linoleic acid.

* * * * *